United States Patent [19]

Wagner et al.

[11] 4,181,737

[45] Jan. 1, 1980

[54] 4-((3-METHOXYPHENYL)AMINO)BENZOIC ACID, A METHOD FOR TREATING HYPERLIPIDEMIA, AND COMPOSITIONS THEREOF

[75] Inventors: Eugene R. Wagner, Carmel; Alfred A. Renzi, Zionsville, both of Ind.

[73] Assignee: The Dow Chemical Company, Midland, Mich.

[21] Appl. No.: 907,078

[22] Filed: May 18, 1978

[51] Int. Cl.² .................... A61K 31/19; C07C 101/60
[52] U.S. Cl. ................................ 424/319; 260/448 R; 260/501.11; 424/287; 424/316; 562/452
[58] Field of Search ......... 560/45; 260/448 R, 501.11, 260/519; 424/287, 316, 310, 319; 562/452

[56] References Cited

U.S. PATENT DOCUMENTS 3,868,416  2/1975  Albright et al. ................. 260/518 R

FOREIGN PATENT DOCUMENTS 7602332  9/1976  Netherlands .

OTHER PUBLICATIONS

Hayes et al., J. Chem. Soc., (1970) p. 1088.

*Primary Examiner*—Richard Raymond
*Attorney, Agent, or Firm*—James W. Ambrosius

[57] ABSTRACT

The compound 4-((3-methoxyphenylmethyl)amino)-benzoic acid and the pharmaceutically-acceptable salts thereof used to treat hyperlipidemia, especially hypercholesterolemia, and pharmaceutical compositions thereof.

3 Claims, No Drawings

4-((3-METHOXYPHENYL)AMINO)BENZOIC ACID, A METHOD FOR TREATING HYPERLIPIDEMIA, AND COMPOSITIONS THEREOF

BACKGROUND OF THE INVENTION

As established by various studies, it is recognized that cholesterol and triglycerides play a major role in the formation of atherosclerotic plaques by accelerating the deposition of blood lipids in the arterial wall.

The compound 4-((4-methoxyphenylmethyl)amino)benzoic acid and the methyl ester thereof have been described in J. Chem. Soc. 8, 1088 (1970). Although, various derivatives of benzoic acid are known to act as hypolipidemic agents in lowering the cholesterol and triglyceride levels in the serum of mammals, the compound 4-((4-methoxyphenylmethyl)amino)benzoic acid shows poor activity as a hypocholesterolemic agent and only moderate activity as a hypotriglyceridemic agent.

SUMMARY OF THE INVENTION

The present invention relates to the compound 4-((3-methoxyphenylmethyl)amino)benzoic acid and the pharmaceutically-acceptable salts thereof. The invention also relates to the use of this compound in lowering serum lipid levels in a mammal, i.e., the serum levels of cholesterol and triglycerides in the mammal, and to the hypolipidemic composition which comprises an effective hypolipidemic amount of the compound 4-((3-methoxyphenylmethyl)amino)benzoic acid or a pharmaceutically-acceptable salt thereof in combination with a pharmaceutically-acceptable carrier.

As used herein, the term pharmaceutically-acceptable salts refer to the acid addition salts of those bases which will not cause an adverse physiological effect when administered to an animal at dosages consistent with good pharmacological activity. Suitable bases thus include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary, and tertiary amines and the like. Also aluminum slats of the instant compounds may be obtained by treating the corresponding sodium salt with an appropriate aluminum complex such as aluminum chloride hexahydrate, etc.

As noted above the subject compound and the pharmaceutically-acceptable salts thereof have shown hypolipidemic activity in mammals. Hypolipidemic activity are used herein refers to the effect of lowering the blood lipid content and in particular the cholesterol and triglyceride content of the serum. The compounds of the present invention are therefore suitable for use in treating serum hyperlipidemia in mammals and in particular are useful for the treatment of hypercholesterolemia and hypertriglyceridemia, that is, abnormally high levels of lipids, cholesterol, or triglycerides, respectively, in the serum. The compounds can be administered orally or parenterally by subcutaneous, intravenous, or intraperitoneal injection or by implantation or the like, oral administration being preferred.

The hypolipidemic amount of the p-benzylaminobenzoic acid compounds to be administered to the mammal, that is the amount which is effective to significantly lower the serum lipid level, can vary depending upon such factors as the particular animal treated, the particular salt of the acid employed, the desired lipid level to be obtained, whether or not the mammal is hyperlipidemic, the period of administration and the method of administration. In general an effective daily dosage range is from about 1 to 400 milligrams per kilogram of body weight, with a daily dosage range of from about 5 to about 15 mg/kg of body weight being preferred.

DETAILED DESCRIPTION OF THE INVENTION

The compound 4-((3-methoxyphenylmethyl)amino)benzoic acid is prepared by known procedures. In one method, the subject compound is prepared by reacting p-aminobenzoic acid in an inert solvent with 3-methoxy benzaldehyde. The resulting Schiff base may be reduced to prepare the corresponding subject compound. A convenient method of carrying out this latter procedure involves mixing about 0.1 mol. of the Schiff base with an excess of ethanol and water. Dilute aqueous sodium hydroxide, for example about 0.1 molar equivalent of the Schiff base, optionally can be added to the mixture. Sodium borohydride, NaBH$_4$, (0.1 mol.) is added at room temperature and stirred until it dissolves. The mixture is then heated to reflux for 1 to 2 hours. The mixture is poured onto ice and acidified. The product may be filtered off as a precipitate and further purified by known procedures as required.

In practicing the method for lowering serum lipid levels in a mammal, the mammal is administered internally a hypolipidemic amount of the subject compound or a pharmaceutically-acceptable salt thereof. The compound of the present invention is particularly useful for lowering the cholesterol level of the serum. Therefore, the present invention is especially directed to a method for lowering serum cholesterol in a mammal by administering internally to said mammal a hypocholesterolemic amount of the subject compound or a pharmaceutically-acceptable salt thereof.

For oral administration, pharmaceutical preparations of the p-amino benzoic acids may be made by following the conventional techniques of the pharmaceutical chemist. These techniques involve granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linquets, powders, capsules, slurries, troches or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate or lactose, disintegrating agents such as maize starch or alginic acid, and lubricating agents such as magnesium stearate may be used.

If a liquid carrier is used, the preparation may be in the form of a soft gelatin capsule, a syrup, a liquid solution or suspension.

The hydrocarbon solubility of most of the compounds of this invention is high enough to allow the use of pharmaceutically-acceptable oils as carriers. For example vegetable or animal oils such as sunflower oil, safflower oil, maize oil or cod liver oil can be used. Glycerine can also be used. With this latter solvent, from 2 to 30 percent water may be added. When water alone is the carrier, or when the solubility of the compound in the oil is low, the preparations can be administered in the form of a slurry.

Emulsion compositions may be formulated using emulsifying agents such as sorbitan trioleate, polyoxyethylene sorbitan monooleate, lecithin, gum acacia or gum tragacanth. Aqueous based suspensions may be prepared with the aid of wetting agents such as polyethylene oxide condensation products of alkylphenols, fatty alcohols or fatty acids with the suspending agents, for example a hydrophilic colloid such as polyvinylpyrrolidone. The emulsions and suspensions may contain conventional excipients such as sweetening agents, flowing agents, coloring materials and preservatives.

The subject compounds can also be incorporated in a nutritive foodstuff such as, for example, margarine, edible oils, casein, carbohydrates and the like. Such nutritive compositions are adapted to be administered as a partial or total diet or as a supplement to the diet. Such compositions preferably contain from about 0.02 or less to about 2.0 or more percent of the active ingredient when administered as the total diet. The compositions can contain higher concentrations of the active ingredient when administered as a supplement.

For parenteral use, the compounds of this invention can be formulated with sterile ingredients, compounded and packaged aseptically. They may be administered intravenously or intramuscularly. Useful solvents for formulation in such use are the polyhydric aliphatic alcohols and mixtures thereof. Especially satisfactory are the pharmaceutically-acceptable glycols, such as propylene glycol, and mixtures thereof. Glycerine is another example of a polyol which is particularly useful. Up to 25-30 percent by volume of water may be incorporated in the vehicle if desired. An 80 percent aqueous propylene glycol solution is a particularly convenient solvent system. A pH range, about 7.4, and isotonicity comparable with body isotonicity, is desirable. Basicity may be controlled by addition of a base as required, and a particularly convenient base is monoethanolamine. It may often be desirable to incorporate a local anesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g. at least 1 percent and preferably at least 5 percent, are preferred as they allow for the easier administration of the compound.

Demonstration of the hypolipidemic activity of 4-((3-methoxyphenylmethyl)amino)benzoic acid was carried out as follows:

The compound was dissolved in acetone, taken up on a silica gel and mixed with normal ground feed to yield concentrations of 0.125 percent of the compound in the animal feed. The treated feed was administered to male Sprague-Dawley strain rats weighing 150-160 grams over a fourteen-day period. A group of six rats were used in the evaluation of the subject compound. Additional groups of control rats receiving untreated feed were used as controls. Following the fourteen-day feeding period, the rats were weighed and killed by decapitation. Blood samples were collected and the liver removed. The relative levels of serum cholesterol and triglycerides in the blood samples were determined by using an automated method employing a Technicon Autoanalyzer ® (Technicon). Taking the average levels of the control rats as standard, the mean results obtained in the treated groups was thereby ascertained. The results are shown in Table I expressed as relative change in values for the treated animals as compared to the control group.

TABLE I

| | |
|---|---|
| Serum Cholesterol | −34%* |
| Serum Triglycerides | −47%* |
| Body Weight | −3%* |
| Liver Weight | +1% |

*All values are expressed as percent change compared to the control group.

The data indicate that the subject compound is an effective hypocholesterolemic and hypotriglyceridemic agent when administered according to the method of the present invention. The minor change in body weight and liver weight indicate that under the conditions of use no significant side effects were observed in these properties.

We claim:

1. The compound 4-((3-methoxyphenylmethyl)amino)benzoic acid and the pharmaceutically-acceptable salts thereof.

2. A method for treating hypocholesterolemia in a mammal which comprises administering internally to the mammal an effective hypocholesterolemic amount of the compound 4-((3-methoxyphenylmethyl)amino)benzoic acid or a pharmaceutically-acceptable salt thereof.

3. A hypolipidemic composition which comprises an effective hypolipidemic amount of the compound 4-((3-methoxyphenylmethyl)amino)benzoic acid or a pharmaceutically-acceptable salt thereof in combination with a pharmaceutical carrier.

* * * * *